United States Patent [19]

Nigro

[11] 4,198,978
[45] Apr. 22, 1980

[54] ADJUSTABLE TAMPON INSERTER

[75] Inventor: Louis V. Nigro, Saugus, Mass.

[73] Assignee: The Gillette Company, Boston, Mass.

[21] Appl. No.: 837,715

[22] Filed: Sep. 29, 1977

[51] Int. Cl.² ............................................. A61F 13/20
[52] U.S. Cl. ..................................... 128/285; 128/270
[58] Field of Search ................. 129/285, 270; 222/309

[56] References Cited

U.S. PATENT DOCUMENTS

| 682,090 | 9/1901 | Lee | 128/263 |
|---|---|---|---|
| 1,724,765 | 8/1929 | McCauley | 222/246 |
| 2,524,195 | 4/1950 | Hoover | 128/263 |
| 2,559,328 | 7/1951 | Thomas | 222/309 X |
| 3,902,493 | 9/1975 | Baier et al. | 128/270 |

Primary Examiner—Robert W. Michell
Assistant Examiner—Milford Juten
Attorney, Agent, or Firm—Richard A. Wise; William M. Anderson

[57] ABSTRACT

A tampon inserter is disclosed of the type comprising an outer cylindrical insertion tube containing a compressed tampon in its proximal end and an inner plunger or piston axially movable within the outer tube for ejecting the tampon out of the proximal end of the insertion tube into the vagina. The outer insertion tube which is rotatable about the plunger is provided with (a) an outwardly extending annular ring to control the depth of insertion of the inserter and (b) an inwardly directed key or finger which depending upon the degree of rotation of the insertion tube about the plunger will extend into one of a plurality of elongated slots of various lengths positioned in the walls of the inner plunger which (slots) control the length of travel of the plunger and thereby provide a means for varying the depth of insertion of the tampon.

2 Claims, 6 Drawing Figures

U.S. Patent  Apr. 22, 1980  4,198,978
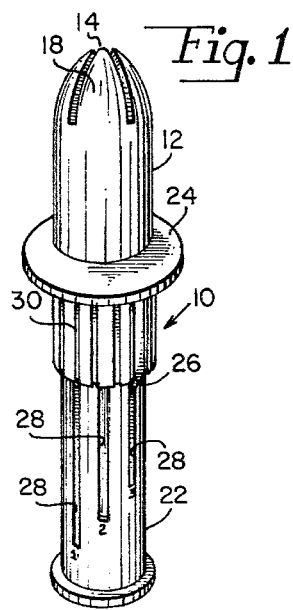
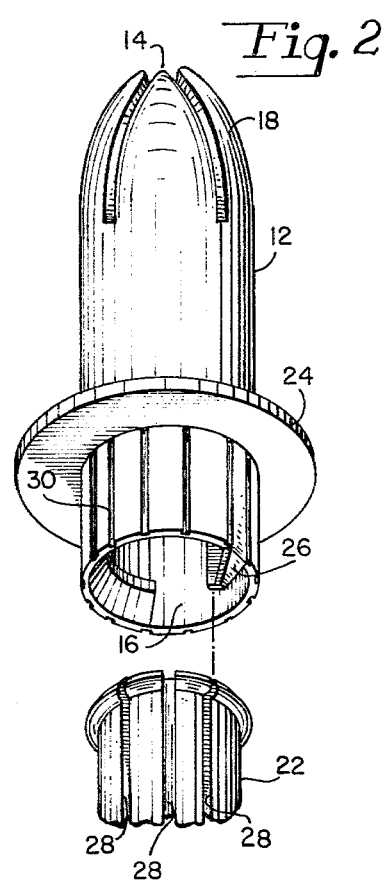
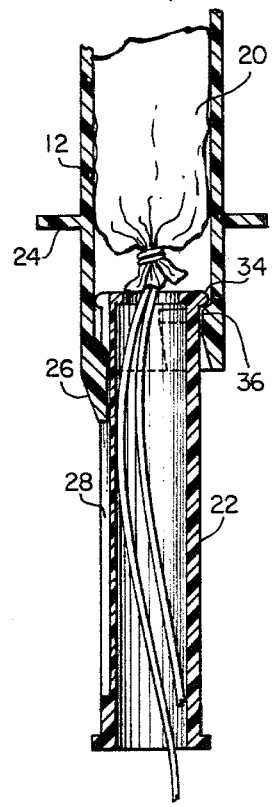
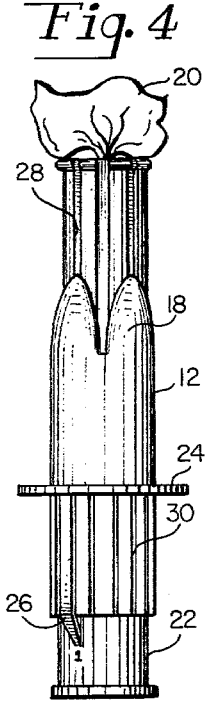
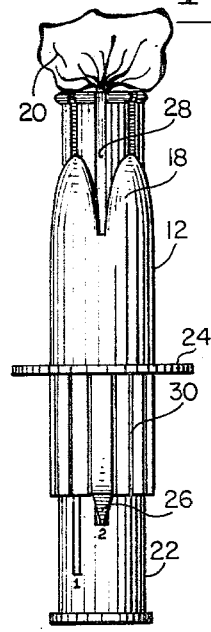
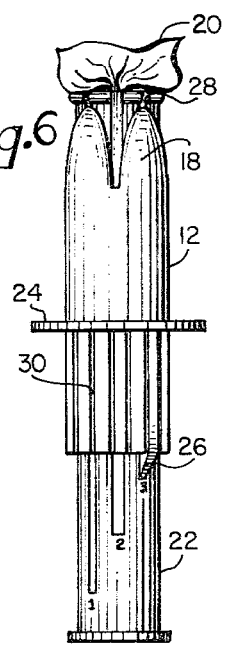

ADJUSTABLE TAMPON INSERTER

In the tampon field the most widely used inserter comprises an outer cylindrical insertion tube having a tampon compressed in its proximal end and an inner plunger or piston axially movable within the outer tube for ejecting the tampon out of the proximal end of the insertion tube into the vagina. In some instances the outer insertion tubes are provided with fixed annular rings which can be used to control the depth of insertion of the tampon by being engaged by the fingers of the user. Although such annular rings in some instances provide good results they are not entirely satisfactory because, as is well known, women vary in size and the depth of insertion of the tampon varies, often causing pain and discomfort and by-pass. The present invention is concerned with providing tampon inserters which have improved means for varying and controlling the depth of insertion of the tampon.

One object of the present invention is to provide tampon inserters of the cylinder-plunger type which have improved means for controlling the depth of insertion of the tampon.

Another object is to provide such an inserter which can be economically produced.

Other objects should be clear from the following detailed description taken together with the claims and drawing wherein:

FIG. 1 is an isometric view of an inserter within the scope of the invention;

FIG. 2 is an exploded isometric view showing the outer insertion tube and a portion of the plunger of an inserter within the scope of the present invention;

FIG. 3 is a partial cross sectional view of an inserter within the scope of the present invention; and FIGS. 4, 5, and 6 are partial front views showing the extent of travel of the plunger at three different settings of the variable depth control means.

Broadly the above objects are achieved with an inserter comprising an outer cylindrical insertion tube having in its proximal end for receiving a compressed tampon and an inner plunger or piston axially movable within the outer tube for ejecting the tampon into the vagina. The outer insertion tube is rotatable around the plunger and is provided with (a) a fixedly attached outwardly extending annular ring and (b) an inwardly directed key or finger which depending on the degree of rotation of the insertion tube about the plunger will extend into one of a plurality of elongated slots of varying lengths provided in the walls of the plunger which (slots) control the length of travel of the plunger and thereby provide means for varying and controlling the depth of insertion of the tampon.

Referring to the drawing and particularly FIGS. 1, 2, and 3, the inserter 10 which, for example, may be made from polyethylene comprises an outer insertion tube 12 having a proximal opening 14 and a distal opening 16. The proximal opening 14 is partially closed by a plurality of inwardly directed tapering flexible flaps 18. As best shown in FIG. 3, said proximal end of the insertion tube 12 is adapted to receive a compressed tampon 20. When axial pressure is applied to the tampon 20 the tips of the flaps 18 are adapted to move outwardly to provide an enlarged opening for ejection of the tampon 20. In the distal end of the inserter 12 there is positioned a cylindrical plunger or piston 22 which telescopically fits inside the distal opening 16 of the insertion tube 12 and is axially movable therein. In addition to being axially movable, the plunger 22 is of such cross section that the insertion tube 12 may be circumferencially rotated about the plunger 22. On the outer surface of the insertion tube 12 there is provided a fixedly attached, outwardly extending annular ring 24 which is adapted to be engaged by the vulva or fingers of the user. Although the ring 24 is shown to be positioned intermediate the proximal and distal ends of the insertion tube 12, it should be understood that it can be positioned at either end of said tube 12 provided it does not interfere with the outward movement of the flaps 18. Attached to the lower portion of the insertion tube there is provided a fixedly attached inwardly extending finger or key 26. The key 26 has sufficient flexibility so as to permit said insertion tube 12 to be rotated about the piston 22 and to permit said key 26 to be inserted into any one of a plurality of elongated axially aligned slots 28 positioned in the walls of the plunger 22. On the lower external surface of the insertion tube 12 there are provided a plurality of axially aligned ridges 30 which serve as finger grips to assist the user in rotating the insertion tube 12 about the plunger. Although it is not shown a circumferential channel may also be provided in the wall of the plunger which (channel) connects with the plurality of elongated slots 28 and is adapted to receive the key 26 and thus facilitate the rotation of the insertion tube 12 about the plunger 22.

As best shown in FIG. 3, the proximal end of the plunger 22 is provided with an outwardly extending annular lip 34 which is adapted to engage an inwardly extending annular shoulder 36 on the insertion tube 12 and thereby prevent said plunger 22 and insertion tube 12 from being accidentally separated.

The operation of the inserters 10 within the scope of the present invention is quite simple and can best be illustrated by reference to FIGS. 4, 5, and 6. As shown in FIG. 4 a woman with a large frame would rotate the insertion tube 12 until the key 26 was positioned in the longest slot 28 (numbered 1) which, as shown, permits the longest travel of the plunger 22. Similarly women of intermediate and slight build would respectively rotate the insertion tube until the key 26 was positioned in slots 28 (numbered 2 and 3) which would permit progressively shorter travel distances of the plunger. As can be appreciated once the user found the proper setting, she could consistently insert the tampon 20 at the proper depth each time.

Having thus described the invention what is claimed is:

1. A tampon inserter having means for varying the depth of insertion of said tampon, said inserter comprising a cylindrical insertion tube having a proximal end and a distal end, said tube being adapted to receive a tampon in said proximal end, an outwardly extending annular ring fixedly attached to the outer surface of said insertion tube, an inwardly extending flexible finger fixedly attached to said insertion tube adjacent the distal end, an elongated plunger which is axially movable within said insertion tube for expelling the tampon, a plurality of elongated sots of varying length in the walls of said plunger, said slots being aligned lengthwise so as to be parallel to the axis of said plunger, and said insertion tube being circumferentially rotatable about said plunger whereby said finger may extend into any of said slots and thereby variably control the extent of axial travel of said plunger.

2. A tampon inserter as defined in claim 1 in combination with a tampon which is disposed within the proximal end of said insertion tube.